US011610513B2

(12) United States Patent
Hanafialamdari et al.

(10) Patent No.: US 11,610,513 B2
(45) Date of Patent: Mar. 21, 2023

(54) BENCHTOP WITHIN-BREATH DYNAMIC LUNG SIMULATOR

(71) Applicant: NovaResp Technologies Inc., Halifax (CA)

(72) Inventors: Hamed Hanafialamdari, Halifax (CA); Matthew Donald Hickey, Vancouver (CA); Lee Ryan Babin, Halifax (CA)

(73) Assignee: NovaResp Technologies Inc., Halifax (CA)

( * ) Notice: Subject to any disclaimer, the term of this patent is extended or adjusted under 35 U.S.C. 154(b) by 672 days.

(21) Appl. No.: 16/678,153

(22) Filed: Nov. 8, 2019

(65) Prior Publication Data

US 2020/0152089 A1    May 14, 2020

Related U.S. Application Data

(60) Provisional application No. 62/758,394, filed on Nov. 9, 2018.

(51) Int. Cl.
*G09B 23/32* (2006.01)
*G09B 23/28* (2006.01)
*A61B 5/091* (2006.01)

(52) U.S. Cl.
CPC ............ *G09B 23/288* (2013.01); *A61B 5/091* (2013.01); *G09B 23/32* (2013.01); *A61B 2562/0247* (2013.01)

(58) Field of Classification Search
CPC ...... G09B 23/288; G09B 23/32; A61B 5/091; A61B 2562/0247

USPC ......................................................... 434/272
See application file for complete search history.

(56) References Cited

U.S. PATENT DOCUMENTS

| | | | |
|---|---|---|---|
| 3,329,390 A | 7/1967 | Hulsey | |
| 4,083,245 A | 4/1978 | Osborn | |
| 5,449,141 A | 9/1995 | Gillett et al. | |
| 5,464,189 A | 11/1995 | Li | |
| 5,584,701 A * | 12/1996 | Lampotang | G09B 23/285 434/262 |
| 7,255,012 B2 | 8/2007 | Hedtke | |
| 2014/0099621 A1* | 4/2014 | Fuchs | G09B 23/288 434/272 |

FOREIGN PATENT DOCUMENTS

EP    2329170 B1    5/2016

OTHER PUBLICATIONS

Czövek et al., "Tidal changes in respiratory resistance are sensitive indicators of airway obstruction in children", Thorax, 2016, 71(10): 907-915.

* cited by examiner

*Primary Examiner* — Robert P Bullington
(74) *Attorney, Agent, or Firm* — Tony Orsi; Bereskin & Parr LLP/S.E.N.C.R.L., s.r.l.

(57) ABSTRACT

There is disclosed a simulation system for simulating a respiratory system. The simulation system includes a variable resistance device that provides a variable resistance to the airflow it receives to simulate a variation in resistance for the respiratory system during breathing and a variable elastance device that provides a variable elastance to the airflow it receives to simulate a variation in elastance for the respiratory system during breathing.

20 Claims, 7 Drawing Sheets

BENCHTOP WITHIN-BREATH DYNAMIC LUNG SIMULATOR

CROSS-REFERENCE

This application claims the benefit of U.S. Provisional Patent Application No. 62/758,394, filed Nov. 9, 2018, and the entire contents of U.S. Provisional Patent Application No. 62/758,394 is hereby incorporated by reference.

FIELD

Various embodiments are described herein that generally relate to lung simulators, and in particular for systems and methods that may be used to simulate breathing.

BACKGROUND

A lung simulator is a device that can be used to model and simulate the respiratory system of an individual or animal. The lung simulators that are currently on the market may be used to model various respiratory conditions and pathologies. The lung simulators may be used to measure various respiratory characteristics such as lung volume and lung pressure as well as pressure along certain airways of the respiratory system. However, lung simulators that are currently on the market do not simulate changes within breath respiratory mechanics.

SUMMARY OF VARIOUS EMBODIMENTS

According to one aspect of the teachings herein, there is provided a variable resistance device for simulating variations of airway resistance during breathing in a lung simulator, the device comprising: an inlet for receiving an input airflow; an outlet for dispelling an output airflow; a channel that is in fluid communication with the inlet and the outlet for receiving the input airflow and providing the output airflow to the outlet; and an adjustable restrictive element disposed within the channel and having an orifice that is adjustable to vary the resistance experienced by air that passes through the channel.

In at least one embodiment, the restrictive device comprises an iris diaphragm having a plurality of members that define the orifice and are moveable to vary the size of the orifice.

In at least one embodiment, the variable resistance device comprises a motor with an output shaft that is coupled to the iris diaphragm for causing the moveable members to move when the motor output shaft is rotated.

In at least one embodiment, the output shaft of the motor is rotated at a frequency that corresponds to a breathing rate.

In at least one embodiment, the variable resistance device comprises a spur gear with a channel that is coupled to the output shaft of the motor, the iris diaphragm comprises a circumferential gear that is coupled to the moveable members and has a first set of teeth that engage a second set of teeth on the spur gear.

In at least one embodiment, the variable resistance device comprises a flexible airway tube that is coupled to the inlet and outlet and is disposed within the adjustable restrictive element and a diameter of the tube is varied by the adjustable restrictive element to vary airflow resistance According to another aspect of the teachings herein, there is disclosed a variable elastance device for simulating elastic properties of a respiratory system, the device comprising: an airtight chamber; an inlet coupled to a first portion of the chamber, the inlet being adapted to receive an input airflow; an outlet coupled to a second portion of the chamber, the outlet being adapted for transmitting an output airflow; and a flexible membrane disposed within the chamber and being shaped to provide an air pathway between the inlet and the outlet, the membrane separating the chamber into first and second sections that are at first and second pressures, respectively, the first pressure being different from the second pressure, wherein the first and second pressures are varied to adjust the elastance of the variable elastance device.

In at least one embodiment, the variable elastance device comprises a pressure tap for varying the second pressure in the second section.

In at least one embodiment, the first section is internal to the membrane and the second section is external to the membrane and internal to the chamber.

In at least one embodiment, the variable elastance device comprises a stent that is disposed within the membrane and coupled to the inlet and the outlet, the stent having rectangular slots for allowing air to flow towards and away from an inner surface of the membrane causing the membrane to expand and contract.

According to yet another aspect of the teachings herein, there is disclosed a simulation system for simulating a respiratory system, the simulation system comprising: a pressure source for providing input airflow; a variable resistance device that is coupled to the pressure source for receiving the input airflow and providing a variable resistance to the input airflow and providing an intermediate airflow, the variable resistance being provided to simulate a variation in resistance for the respiratory system during breathing; a variable elastance device that is coupled to the variable resistance device for receiving the intermediate airflow after and providing a variable elastance to the intermediate airflow and providing an output airflow, the variable elastance being provided to simulate a variation in elastance for the respiratory system during breathing; and a lung simulator that is coupled to the variable elastance device for receiving the output airflow and adding a volume of air for aiding in simulation of the respiratory system.

In at least one embodiment, the variable resistance device is defined in according with any of the embodiments described herein.

In at least one embodiment, the variable elastance device is defined according with any of the embodiments described herein.

In at least one embodiment, the variable resistance device is adapted to provide a selected resistance for simulating a respiratory system experiencing a respiratory condition.

In at least one embodiment, the variable elastance device is adapted to provide a selected elastance for simulating a respiratory system experiencing a respiratory condition.

In at least one embodiment, the respiratory condition comprises at least one of asthma, sleep apnea, emphysema and chronic obstructive pulmonary disorder.

In at least one embodiment, the system comprises multiple branches, each branch comprising a variable resistance device having a variable resistance and/or a variable elastance device having a variable resistance elastance.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices, systems or methods having all of the features of any one of the devices, systems or methods described below or to features common to multiple or all of the devices, systems or methods described herein. It is possible that there may be a device, system or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, fluidic or electrical connotation. For example, as used herein, the terms coupled or coupling can indicate that two elements or devices can be directly connected to one another or connected to one another through one or more intermediate elements or devices via an electrical signal, electrical connection, a mechanical element, a fluid or a fluid transport pathway depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation does not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

The example embodiments of the devices, systems or methods described in accordance with the teachings herein may be implemented as a combination of hardware and software. For example, the embodiments described herein may be implemented, at least in part, by using one or more computer programs, executing on one or more programmable devices comprising at least one processing element and at least one storage element (i.e. at least one volatile memory element and at least one non-volatile memory element). The hardware may comprise input devices including at least one of a touch screen, a keyboard, a mouse, buttons, keys, sliders and the like, as well as one or more of a display, a speaker, a printer, and the like depending on the implementation of the hardware.

It is important to simulate changes within breath respiratory mechanics. For example, these changes can include: (1) changes in airway diameter that varies resistance within each breath; and (2) changes in lung elastance that varies within each breath. Advantageously, in one aspect, in accordance with the teachings herein there is provided a variable resistance device (also known as an adjustable resistance device) that can be used to simulate time-variations of airway resistance during breathing for an individual's respiratory system. In another aspect, in accordance with the teachings herein there is provided a variable elastance device (also known as an adjustable elastance device) that can be used to simulate time-variations of elastic properties of an individual's respiratory system. These devices are not available in conventional lung simulators that are currently on the market.

Accordingly, the subject matter of the present application addresses a number of the aforementioned issues with conventional lung simulators. For example, at least one of the variable resistance and variable elastance devices described herein can be used in a lung simulator to simulate time-variations of resistance and elastance of a respiratory system that allows for simulating within breath respiratory mechanics. For example, changes within breath include changes in the radius of airways and elasticity of the whole lung within a single breath. The systems that are currently on the market have a single orifice or mesh resistance that is constant and does not vary within breath. The same issue applies to elastance systems that are currently on the market. In this case these systems have a spring with a specific spring constant that does not vary. The embodiments described herein solves both of these issues. Accordingly, the present subject matter improves the function of existing simulators by introducing at least one of variable resistive and elastic components that can provide realistic simulation of different respiratory conditions and diseases.

The variable resistance and variable elastance devices described herein can be used in a variety of applications. For example, for simulating realistic respiratory scenarios these apparatus, either separate or together, can be provided as add-on devices for benchtop lung simulators that can be used in hospitals and research labs that need to simulate breathing issues. For example, at least one of the variable resistance and variable elastance devices can be used to train physicians, anesthesiologists and other medical staff that need to be trained to react to different respiratory conditions. At least one of these devices can also be used by research labs that are testing different therapy regimens or researching respiratory diseases at the bench. Accordingly, at least one of these devices may be used to develop respiratory medical technologies that can be better tested analyzed before progressing to animal/human trials.

Figure 1:
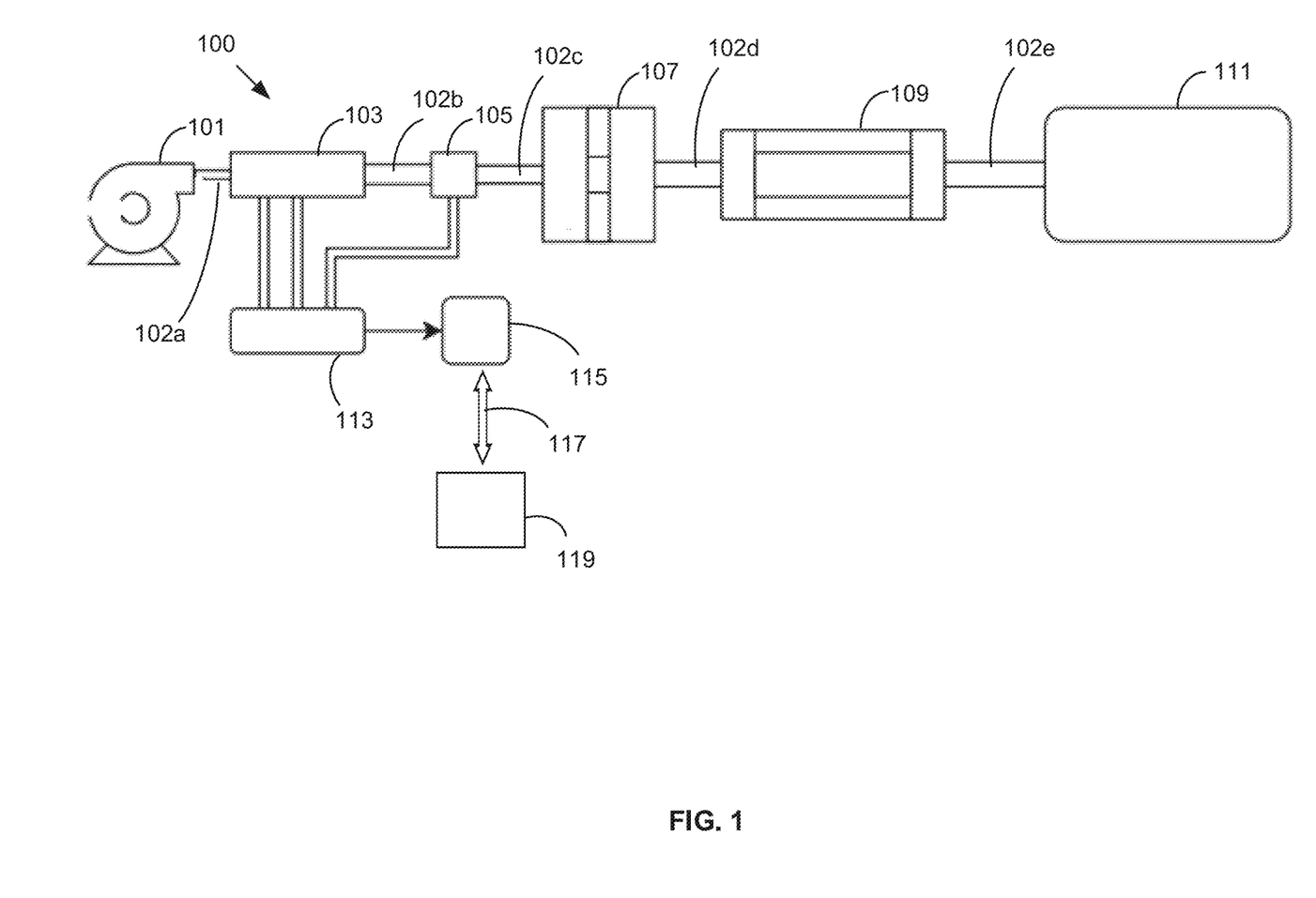
FIG. 1 illustrates an example embodiment of a respiratory system for simulating breathing in accordance with the teachings herein.

Referring now to FIG. 1, there is shown an example embodiment of a respiratory system 100 for simulating breathing in an individual's or an animal's respiratory system in accordance with the teachings herein. The system 100 includes a pressure source 101, an airflow sensor 103 (e.g. a pneumotachograph), a pressure sensor 105 (e.g. a pressure tap), a variable resistance device 107, a variable elastance device 109, a lung simulator 111, a signal conditioning unit 113 (e.g. an airflow sensor amplifier, and a pneumotachograph amplifier), a data acquisition unit 115 and several airflow pathways (e.g. airflow channels 102a-102e) for interconnecting various elements of the respiratory system 100 together. These elements can be preferably miniaturized or scaled up in size depending on the application for which they are used. For example, in some embodiments, the variable elastance device 109 can be miniaturized to be a small tube that is inside of another tube.

A computing device 119 (e.g. a computer, a controller, etc.) can be connected to the data acquisition unit 115 through a communication link 117. The communication link 117 can be a wired and/or wireless network. The computing device 119 can be configured to control the operation of the pressure source 105 and/or the variable elastance device to perform simulations under certain respiratory conditions. The computing device 119 can also be configured to analyze measurement data from the data acquisition unit. The measurement data can include airflow and pressure measurements that are sensed by the airflow sensor 103 and the pressure sensor 105, respectively, and then pre-processed by the signal conditioning unit 113. The computing device 119 typically includes at least one processor, a memory device including temporary and persistent memory elements, and a communications unit including at least one of a serial communications port, a parallel communications port, a USB port, a wireless radio and a Bluetooth unit.

Air, or another gaseous medium having a different viscosity that maybe helpful for simulating different respiratory conditions, can be injected into the system 100 by the pressure source 101. The injected air can travel from the pressure source 101 to the airflow sensor 103 through the air flow channel 102a. The airflow channel 102a (as well as the airflow channels 102b-102e) can be a tube that is made of plastic, rubber, metal, glass and/or any other suitable materials. The airflow channels may also be referred to as air channels, air pathways, airways or airflow pathways. The airflow sensor 103 can measure the amount of air flowing through the system 100 and/or the airflow channel 102a. The airflow sensor 103 can also measure the mass of air flowing through the system 100 per unit of time. The airflow sensor 103 can be connected to the signal conditioning unit 113.

The pressure sensor 105 is connected to the airflow sensor 103 through the airflow channel 102b. The pressure sensor 105 measures the pressure of air flowing through the system 100. Pressure is an expression of the force required to stop the air from expanding, and is usually stated in terms of force per unit area. The pressure sensor 105 can also be used to indirectly measure other variables such as airflow and speed. The pressure sensor 105 can be also connected to the signal conditioning unit 113.

The signal conditioning unit 113 can be connected to both the airflow sensor 103 and the pressure sensor 105. The signal conditioning unit 113 can filter and amplify the measured signals from the airflow sensor 103 and/or the pressure sensor 105 to provide preprocessed signals. The signal conditioning unit 113 is coupled to the data acquisition unit 115 which receives the preprocessed signals and digitizes them using an Analog to Digital Convertor (ADC). The digitized preprocessed signals are then sent to the computing device 119. The data acquisition unit 115 can also include a Digital to Analog Convertor (DAC) so that digital control signals that are sent by the computing device 119 to the data acquisition unit 115 can be converted to analog control signals that are then routed to certain elements of the system 100 for controlling the operation and/or simulation performed by the system 100. In some embodiments, the functions of the signal conditioning unit 113 and the data acquisition unit 115 can be integrated into and implemented by a microcontroller, which may be separate from or integrated within the computing device 119.

The variable resistance device 107 is used for simulating time variations of resistance of airways of the respiratory system 100 during breathing. The variable resistance device 107 can be a time-varying oscillatory resistive valve. The variable resistance device 107 is coupled to the pressure sensor 105 via the airflow channel 102c.

The variable elastance device 109 is used for simulating time-variations of elastic properties of a respiratory system that simulates the time-variations of elastic properties of the respiratory system 100 during breathing. The variable elastance device 109 can be a time-varying oscillatory compliance chamber. The variable elastance device 109 is coupled to the variable resistance device 107 via the airflow channel 102d.

The variable resistance device 107 and the variable elastance device 109 can be used simultaneously or separately to simulate different diseases (e.g. for asthma). Accordingly, while FIG. 1 shows that both devices 107 and 109 are connected to the system 100 it is noted that there can be some embodiments in which only one of the devices 107 and 109 is connected to the system 100.

The lung simulator 111 can include an air chamber with a volume for receiving and dispelling an exchangeable gas. However, the air chamber does not expand and contract. Therefore, the radius of the air chamber does not vary, and the resistance of the air chamber does not vary.

For example, the lung simulator 111 can be a bucket or empty-volume that is used to add a small amount of air volume at high pressure to the system 100. For example, the lung simulator 111 can be a bucket that has a constant volume that does not vary. As another example, the lung simulator 111 can be a piston with a variable and controllable volume. The lung simulator 111 can be made of plastic, rubber or any other suitable materials. As shown in FIG. 1, the lung simulator 111 is coupled to the variable elastance device 109 by the airflow channel 102e. The lung simulator 111 can be a bucket/empty-volume that is commonly used to add air volume to the bench-top set up, or it can be a piston such as ASL5000™ of Ingmar Medical™ and Pneumolung™ of Michigan Instruments™. In both cases, this allows the lung simulator 111 to add a constant or mean compliance to the system 100.

Referring now to FIGS. 2A-2E, shown therein are diagrams of an example embodiment of an adjustable resistance device 107 and parts thereof. The adjustable resistance device 107 can be used with the respiratory system 100 of FIG. 1 to simulate time-variations of airway resistance during breathing in accordance with the teachings herein. The adjustable resistance device 107 can be a time-varying oscillatory resistive valve. The adjustable resistance device 107 includes a variable restrictive element for providing a time-varying resistance to the airflow through the device 107. In this example embodiment, the adjustable resistance device 107 includes an adjustable iris diaphragm, which may be implemented using a motorized valve, that changes its radius at a selected frequency of breathing thereby providing a time-varying resistance to the airflow through the adjustable resistance device 107. However, it should be understood there can be alternative embodiments of an adjustable resistance device that uses an orifice with a diameter that is variably adjustable either manually or in an automated/motorized manner.

The adjustable resistance device 107 includes a casing or housing that is mounted on a base 201. The casing can be sealed air-tight. For example, the sealed airtight casing can be 3D printed using an ABS type compound. The adjustable resistance device 107 includes an inlet 206 at one end and an outlet 216 at the other end. Both the inlet 206 and the outlet 216 can include attachments for connecting the adjustable resistance device 107 to other devices or tubes.

The adjustable resistance device 107 includes a conduit or channel 203 that runs along the longitudinal axis of the adjustable resistance device 107 and can receive a tube (not shown) that provides an airflow channel that allows for the circulation of air through the adjustable resistance device 107. Accordingly, the tube is in fluid communication with the inlet 206 and the outlet 216. In this example embodiment, the inlet 206 is disposed at a first end of the conduit 203 and the outlet 217 is disposed at a second end of the conduit 203. The tube that defines the airflow channel has circumferential wall that surrounds a hollow interior space. The tube can be made of rubber, plastic, PVC or any suitable materials. The tube of the adjustable resistance device 107 can be removable. In the event a different diameter for the tube is needed, a user can remove the tube and replace it by a tube with the desired diameter. The tube can be 3D printed.

The length of the conduit 203 can vary between about 50 mm to about 500 mm. Alternatively, the length of the conduit 203 can be between about 150 mm to about 400 mm. In another alternative embodiment, the length of the conduit 203 can be between about 250 mm to about 300 mm.

The length of the tube can be about 275 mm. In some embodiments, the tube can have an inside diameter of about 12 mm. Alternatively, in some embodiments, the tube can have an inside diameter between about 8 mm and about 16 mm. Alternatively, in some embodiments, the tube can have an inside diameter between about 4 mm and about 20 mm. These various tubes can be selectively used to allow for modelling very small to medium airways to very large airways.

The adjustable resistance device 107 can exist in two main configurations. The first configuration is as shown in the figures where the resistance is caused by the iris contracting and expanding around the air flow to create the time varying resistance. Alternatively, a very thin rubber tube can be suspended from the inlet 206 to the outlet 216 such that is passes through the orifice of the iris. The tube allows the air flow to pass through it. The diameter of the orifice of the iris diaphragm can then be reduced such that the edges defining the orifice clamp down on and decrease the diameter of the tube to change resistance to airflow therethrough.

Figure 2A:
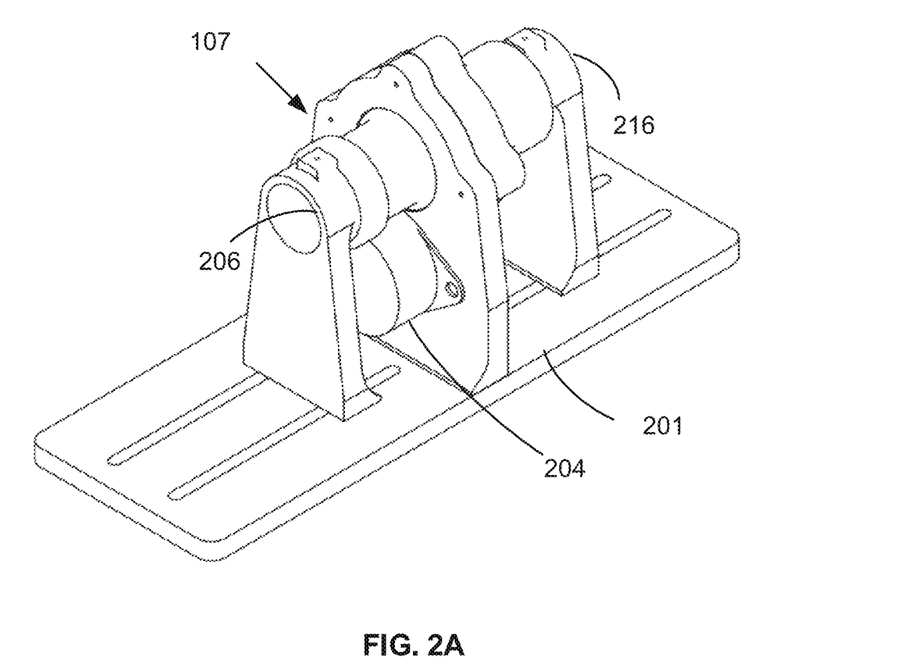
FIGS. 2A-2E illustrate diagrams of an example embodiment of an adjustable resistance device and certain components that can be used with the respiratory system of FIG. 1 to simulate time-variations of airway resistance during breathing and parts thereof in accordance with the teachings herein.
Figure 2B:
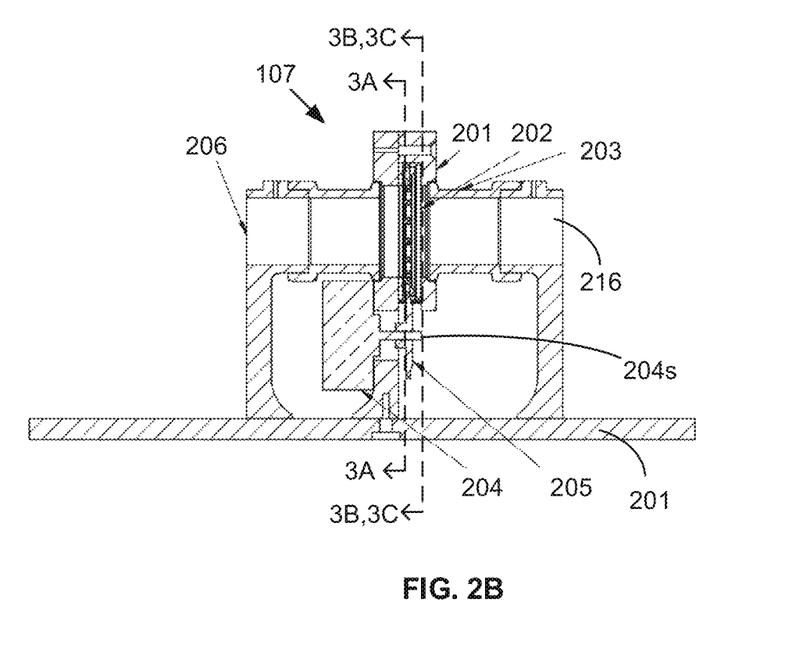

The conduit/channel 203 includes a slot at a mid-portion thereof for receiving a restrictive element that provides for an adjustable resistance to airflow though the adjustable resistance device 107. For example, the resistive element can be an iris diaphragm 202 that provides an adjustable aperture in the airflow channel 203. A spur gear and/or a motor can be connected to the restrictive element to vary the diameter of the iris. For example, as shown in FIG. 2B, the iris diaphragm 202 is coupled to a motor 204 which can be used to change the diameter of the orifice of the iris diaphragm 202 thereby providing a time varying resistance to the air that flows through the adjustable resistance device 107.

An example of the iris diaphragm 202 is shown in FIGS. 2A-2D. The iris diaphragm 202 includes a series of members 215 (e.g. leaves, blades) that are radially positioned such that they are moveable and their position can be adjusted mechanically. The members 215 are disposed so that members 215 that are adjacent to one another overlap one another by a certain amount. Therefore, the members 215 collectively form an opening/orifice 213 at the center of the iris diaphragm 202. When the amount of overlap between members 215 that are adjacent to one another increases, the opening 213 at the center of the iris diaphragm 202 becomes bigger as is shown in FIG. 3B where the iris diaphragm 202 has a larger opening 213a. Conversely when the amount of overlap between members 215 that are adjacent to one another decreases, the opening 213 at the center of the iris diaphragm 202 becomes smaller as is shown in FIG. 3C where the iris diaphragm has a smaller opening 213b.

The outside rim of the iris diaphragm 202 can be made from steel or any other suitable materials. The moveable members 215 of the iris diaphragm 202 can be made of plastic or any other suitable materials. In some embodiment the iris diaphragm 202 can be constructed such that its opening 213 can vary between about 2 mm to about 22 mm in diameter to simulate different amounts of airway resistance. In testing thus far, this range has been more than sufficient to complete laboratory respiratory tests for simulating different respiratory conditions. For example, asthma can be simulated using the adjustable resistance device 107. In this case, the diameter change in asthmatic children is smaller than in asthmatic adults. As another example, the adjustable resistance device 107 can be used to simulate obstructive sleep apnea where the airway orifice of the iris diaphragm closes to simulate obstruction. In another example, the adjustable resistance device 107 can be used to simulate snoring where the airway orifice is oscillating (changes in radius) at the snoring frequency.

Figure 2C:
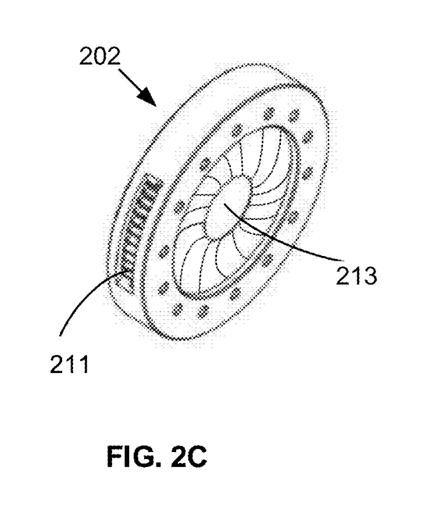
Figure 2D:
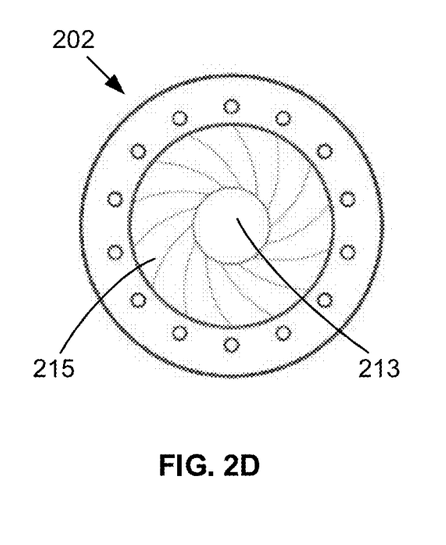

Referring now to FIGS. 2B to 2E, the adjustable resistance device 107 includes a motor 204 that has an output shaft 204s that is coupled to a spur gear 205 which in turn engages a circumferential gear 211 of the iris diaphragm 202 to control the diameter of the opening 213. The motor 204 can be a steeper motor. The angular position of the motor 204 can be controlled though the progression of steps that the motor 204 rotates through. As each phase of the motor 204 is energized, it causes the motor 204 to progress by one step (which in this example embodiment is 7.4 degrees, but can be another amount in other embodiments). The output shaft 204s engages a channel 205c of the spur gear 205 so that the output shaft 204 can rotate the spur gear 205. As the motor 204 rotates the output shaft 204s, it turns the spur gear 205 (e.g. a brass pinion) that interacts with the teeth of the circumferential gear 211 at the periphery of the iris diaphragm 202. The spur gear 205 is shown in both FIGS. 2B and 2E. The circumferential gear 211 of the iris diaphragm 202 is shown in FIG. 2C. The circumferential gear 211 has rectangular channels or slots through which small circular rubber pieces that are connected to the moveable members 215 (i.e. leaves) rotate and slide within those channels as the gear 205 rotates, causing the moveable members 215 to increase their overlap of each other or decrease their overlap of each other depending on the direction of rotation of the gear 205. Therefore, by rotating the circumferential gear 211, the moveable members 215 are moved such that the diameter of the iris opening 213 can be adjusted to be larger or smaller depending on the direction that the output shaft 204s of the motor 204 is rotating.

Figure 2E:
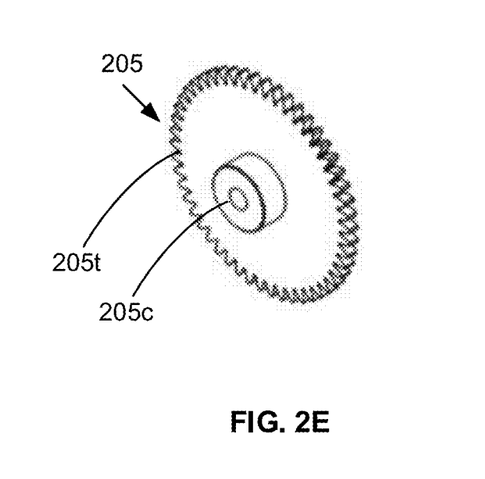

Various gear ratios between the circumferential gear 211 and the spur 205 may be used. For example, a higher gear ratio may be used for more finely controlling the change in the diameter of the opening 213 of the iris diaphragm 202 as the output shaft 204s of the motor 204 is rotated. For example, a gear ratio of 1.5 can be used.

Figure 3A:
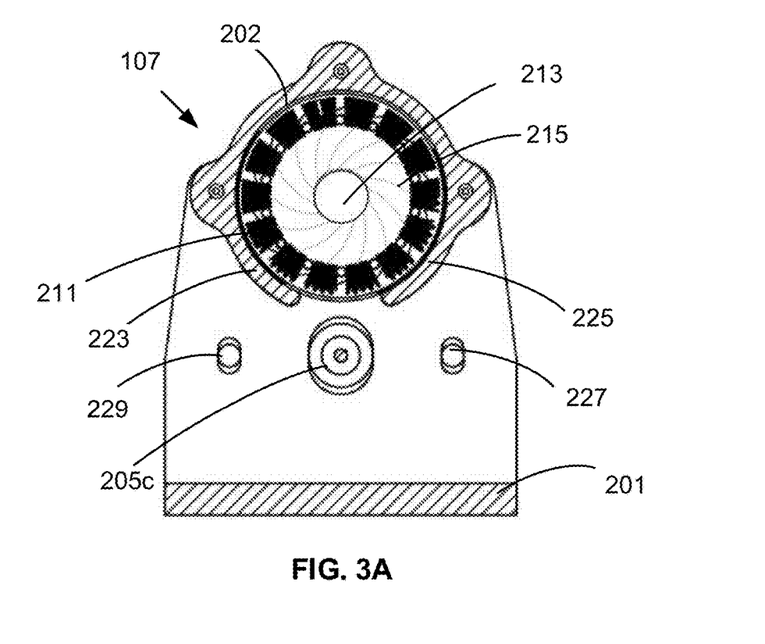
FIGS. 3A-3C show cross-sectional views of the device of FIGS. 2A-2E.
Figure 3B:
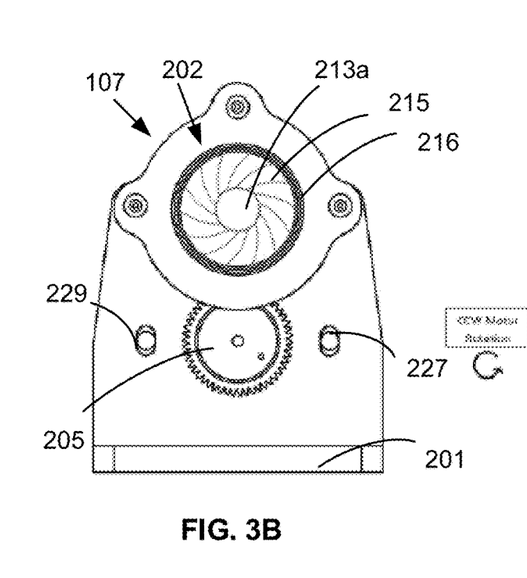
Figure 3C:
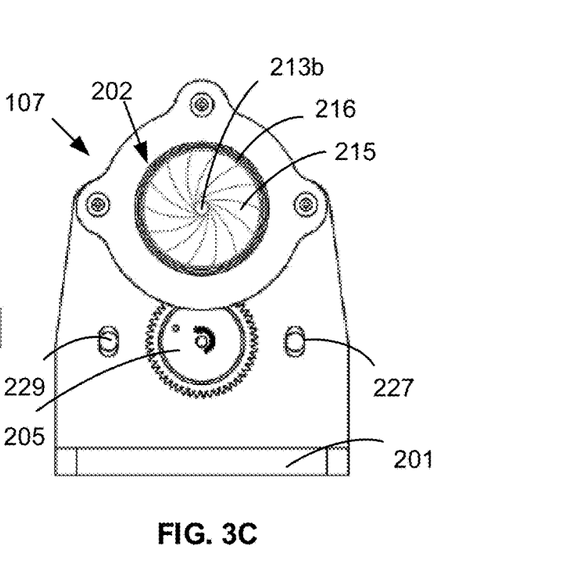

Referring now to FIGS. 3A-3C, there is shown a cross-sectional view along a plane that intersects the spur gear (in FIG. 3A) and another plane that interests the iris diaphragm 202 of the apparatus 107 (in FIG. 3B-3C). As shown in FIGS. 3B-3C, the spur gear 205 interacts with the circumferential gear 211 of the iris diaphragm 202 as the spur gear 205 is rotates. For example, teeth on the spur gear 205 engage teeth of the circumferential gear 211 of the iris diaphragm 202. The spur gear 205 can be toothed all the way around.

In an alternative embodiment, it is possible to operate the iris diaphragm manually without using the gear train provided by the spur gear 205, and the circumferential gear 211. In such embodiments, a small steel lever can be screwed into the circumferential gear 211 and used to rotate the circumferential gear 211 thereby adjusting the position of the moveable members 215.

Referring now to FIG. 3A, there are shown two slots 223 and 225 that are in part of the structural backing of the device 207. There are mating extrusions from a cap 216 (see FIGS. 3B and 3C) that fits over the iris diaphragm 202 and engages with the slots 223 and 225 to securely fasten the iris diaphragm 202 in place to a structural backing of the adjustable resistance device 207. The edges of the iris diaphragm 202 can be covered in silicone to create an airtight seal.

FIGS. 3B and 3C show the iris diaphragm 202 with different sized orifices 213a and 213b, respectively. In this example embodiment, as the circumferential gear 211 is rotated clockwise, the diameter of the orifice 213 of the iris diaphragm 202 is decreased and when the circumferential gear 211 is rotated counter-clockwise the diameter of the orifice 213 of the iris diaphragm 202 is increased. As explained earlier, the diameter of the orifice 213 of the iris diaphragm 202 can be changed by varying the amount of overlap for the moveable members 215 that radially extend towards the center of the orifice 213.

Changing the diameter of the orifice 213 of the iris diaphragm 202 creates a variable resistance when air is flowing inside the channel 203. Therefore, changing the diameter of the orifice 213 can be used to simulate changing breathing airways, which are known to alter in disease. For example in asthma, this time-varying resistance increases. Therefore, to model asthma, the radius of the orifice can be altered in the same frequency as breathing. For example, in an adult patient, this frequency may be 0.3 Hz. In a healthy patient, this alteration in resistance is much smaller.

As mentioned, the frequency at which the moveable members 215 are moved to vary the size of the orifice 213 corresponds to the breathing frequency that is being simulated for the respiratory system 100. The frequency is controlled by changing the time delay between the steps of the stepper motor 204. If the time delay is high then the angular velocity of rotation of the output shaft 204s of the motor 204 will be low and therefore the simulated breathing frequency will be low. The position of the output shaft 204s of the motor 204 relative to the diameter of the orifice 213 of the iris diaphragm 202 is programmable by adjusting the number of steps that the motor 204 rotates through in a cycle. One cycle can be considered to be one oscillation of the variable resistive device 107 which includes the steps used to bring the orifice 213 of the iris diaphragm 202 from its maximum diameter to its minimum diameter. Smooth variations can be accomplished via micro stepping, which is a technique that is used to increase motor resolution by creating a smooth transition between stepper motor phases. This can reduce the apparent step size from about 7.4 degrees to about 1 degree for even finer control over the rate in which the diameter of the orifice 213 is varied. Bolts 227 and 229 can be used to fasten the housing of the motor 204 to the housing of the device 207 and maintain the motor 204 in place.

Figure 4A:
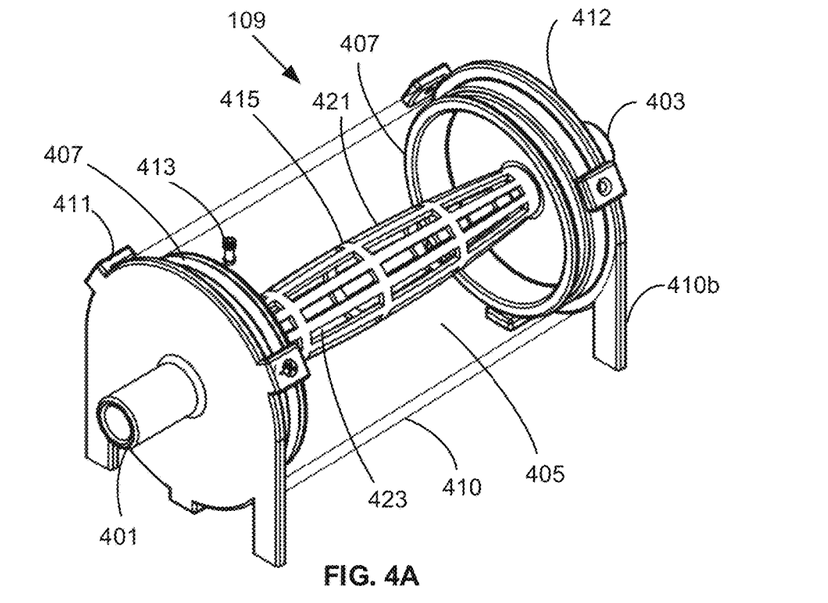
FIGS. 4A-4B illustrate diagrams of an example embodiment of an adjustable elastance device that can be used with the respiratory system of FIG. 1 to simulate time-variations of elastic properties of airway resistance during breathing in accordance with the teachings herein.
Figure 4B:
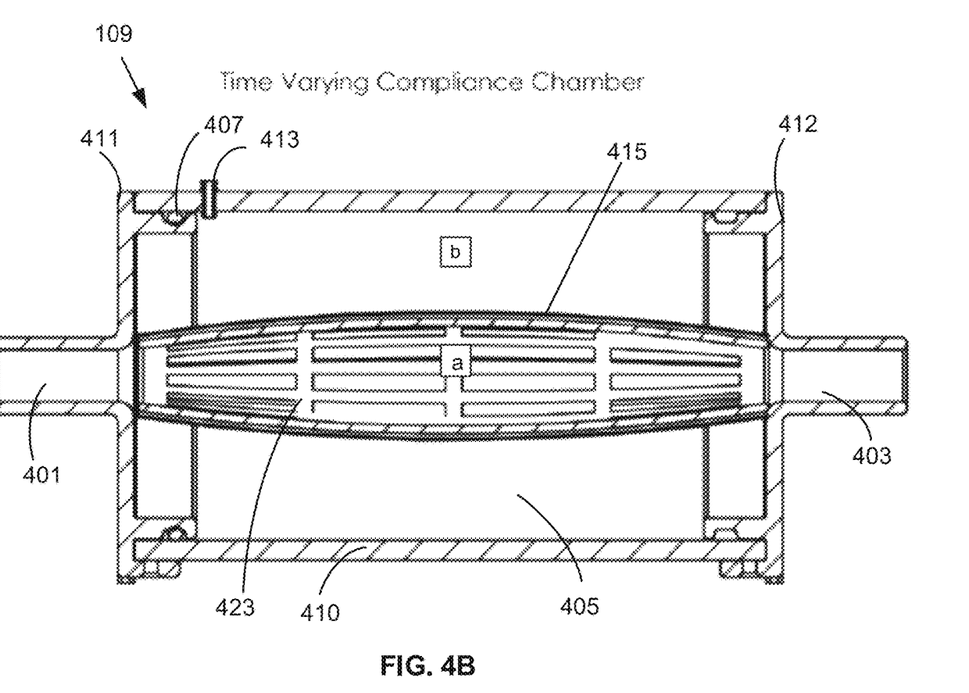

Referring now to FIGS. 4A and 4B, there is shown an example embodiment of the adjustable elastance device 109 that can be used to simulate time-variations of elastic properties of the respiratory system 100 in accordance with the teachings herein. In this example embodiment, the adjustable elastance device 109 employs an airtight chamber having regions at different pressures to provide a compliance variation for a flexible material that separates the two sections. However, it should be understood there can be alternative embodiments of an adjustable elastance device that uses a different design but employs the use of two areas in a device where the two areas are at different pressures for varying an element of the device to vary elastance. In some embodiments, the adjustable elastance device 109 includes a motorized structure or piston that pushes air into and out of a compliance chamber to change the compliance (which is the inverse of the elastance) at the frequency of breathing by changing the pressure difference between the two areas (e.g. sections a and b) which is discussed in more detail below.

The adjustable elastance device 109 includes a housing 410 that are coupled to legs 410b (only one of which is labelled for simplicity) to provide a support for the adjustable elastance device 109. The adjustable elastance device 109 has an inlet 401 at a first end and an outlet 403 at a second end. Both the inlet 401 and the outlet 403 can include attachments for connecting the adjustable elastance device 109 to other devices or airflow pathways (e.g. tubes).

As more clearly seen in FIG. 4B, the housing 410 includes a chamber 405 that is divided into two sections, sections a and b, each with its own pressure. Sections a and b can be separated by a membrane 415. The membrane 415 is generally thin and flexible so that it can expand and contract. The membrane 415 may be made from rubber or another suitable material.

The housing 410 is made from a rigid material that has an appropriate thickness to withstand changes in pressure in section b with respect to the external environment of the device 109. The housing 410 can be clear such that the expansion and contraction of the rubber membrane 415 is observable to a user which is helpful in cases where troubleshooting is performed during simulation. For example, if the membrane 415 inflates to failure, or if the membrane 415 is punctured and/or rendered inoperable, the user can visually inspect the chamber 405 to check for these situations. The housing 410 can be made from clear Acrylic.

There are removable end caps 411 and 412 that are disposed at opposite ends of the adjustable elastance device 409 and are removably coupled to the housing 410. The two end caps 411 and 412 form an airtight seal with the housing 410. A seal 407, such as a rubber O-ring, can also be used to maintain an airtight seal between the interior of the chamber 405 that is at a pressure which is different than the atmospheric pressure that is exterior to the device 109. The ends caps 411 and 412 can be made from machined UHMW polyethylene.

In some embodiments, the adjustable elastance device 109 may also include a pressure attachment site 413 (e.g. a Luer lock) on the housing 410. The pressure attachment site 413 may be used to monitor the internal pressure of section b of the cavity 405 of the device 109. Alternatively, the pressure attachment site 413 may be used to relieve pressure or to vary the pressure within the cavity 405 under certain circumstances. For example, to simulate a disease, the pressure within section b of the cavity 405 can be varied sinusoidally. As another example, the pressure within section b can be kept at a constant level to simulate a stiff lung.

As shown in FIGS. 4A and 4B, a stent 423 is disposed inside the membrane 415 and therefore the stent 423 is inside section a. The stent 423 is in fluid communication with both the inlet 401 and outlet 403. The stent 423 may be made from 3D printed material such as an ABS type compound or plastic. There are slots (e.g. rectangular slots) that are cut into the frame of the stent 423 which let air pass through the stent to the membrane 415. The geometry, size, and number of slots for the stent 423 can be varied if desired.

The membrane 415 covers the stent 423 and defines an airflow pathway for air to flow from the inlet 401 to the outlet 403. The membrane 415 can be made of elastic material or rubber material such that it can deform under a pressure load. The membrane 415 may be made of clear material so that the stent 423 can be visually checked to make sure there are not any issues. The thickness and elasticity of the membrane 415 can affect the amount of deformation when there is a pressure difference between sections a and b of the chamber 405. The stent 423 can provide support for the rubber membrane 415 when the pressure in section b is higher than the pressure in section a so that the membrane 415 does not collapse on itself.

When air flows inside the air pathway of the adjustable elastance device 109, the air flows from the inlet 401 to the stent 423, through the slots of the stent 423 into the space between the outer surface of the stent 423 and the inner surface of the membrane 415 and then through the outlet 403 of the adjustable elastance device 109. The membrane 423 can expand or contract due to the difference in pressure in sections a and b. Since the membrane 415 is flexible, its elasticity can be varied at a breathing rate which may be that of a normal respiratory system or another breather rate for simulating a respiratory system that is diseased. Accordingly, the membrane 423 may be moveable (e.g. contract) between a first position during inhalation, and a second position during exhalation and then expand again to the first position during the next inhalation.

Elasticity can be defined as the relationship between pressure and volume (i.e. a given amount of pressure increase causes a certain amount of volume increase). The pressure in section a can be caused by the flow of air through the adjustable elastance device 109. The pressure in section a can be changed sinusoidally at the frequency of breathing. Therefore, the effective pressure that the system 100 uses to measure elasticity is the difference of pressure between sections a and b. Since the pressure in section a is changing at the breathing rate, so is the elasticity. Therefore, air can be injected in an oscillatory manner through the stent 423 so that the membrane 415 that covers the stent 423 can expand and contract in the same fashion as a person's lungs expand and contract.

Figure 5A:
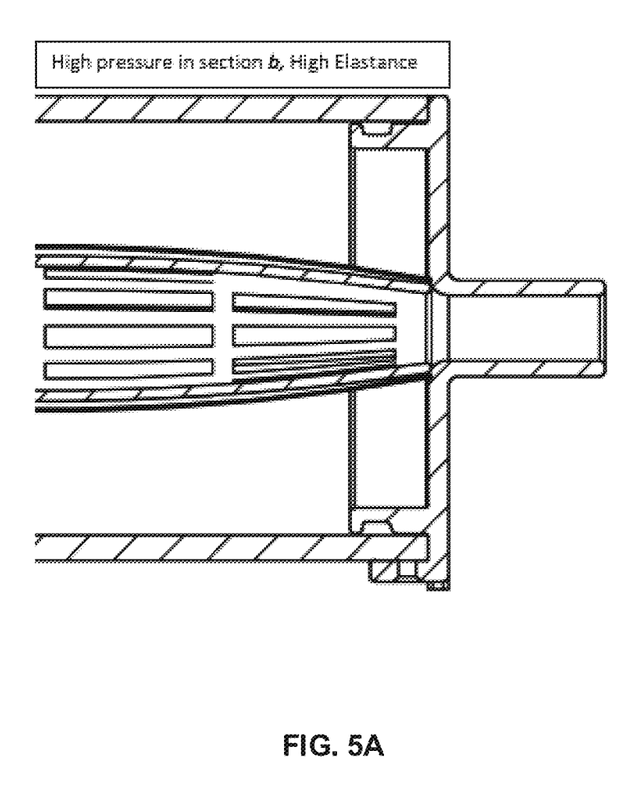
FIGS. 5A and 5B illustrate variations in pressure and elastance for the device of FIGS. 4A-4B.
Figure 5B:
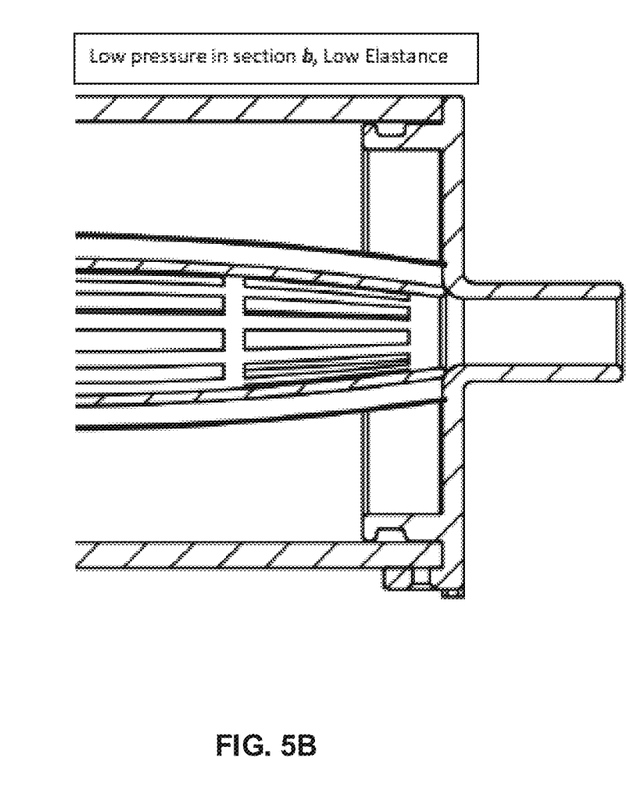

FIGS. 5A and 5B show a change in pressure and elastance in section a and changes in the membrane diameter. FIG. 5A shows a higher pressure in section b relative to the pressure in section a, which results in an increase in elastance for the adjustable elastance device 109. In this case, the membrane 415 now more closely surrounds the stent 423 and it is harder for the membrane 415 to expand. FIG. 5B shows a lower pressure in section b relative to section a, which results in a decrease in elastance for the adjustable elastance membrane 415. In this case, the space between the inner surface of the membrane 415 and the exterior surface of the stent 423 is larger and it is easier for the membrane 415 to expand.

The pressure in section a can be measured using an upstream pressure tap and a pressure sensor, such as the pressure sensor 105. The pressure in section b is changed by pumping air into or out of the chamber 405. There can be a second pressure tap (not shown) that is only used when it is required to measure at what point in the pump's progression the maximum required pressure is reached. After this is determined, the second tap is sealed and not used. For example, in at least one embodiment there can be two outlets (e.g. taps) that are connected to section b, both with Luer locks. One tap is used to push air into and out of section b of the chamber 405 to change the pressure sinusoidally, and the other tap can be used to monitor the pressure in section b.

The pressure in section b can change sinusoidally because air can be pumped into and out of the chamber 405 at a sinusoidal rate. The rate at which air is pumped into the chamber 405 or removed from the chamber 405 can, but is not limited to, correspond to the rate at which the orifice 213 of the iris diaphragm 202 changes in diameter (e.g. oscillates between two different sizes).

Figure 6:
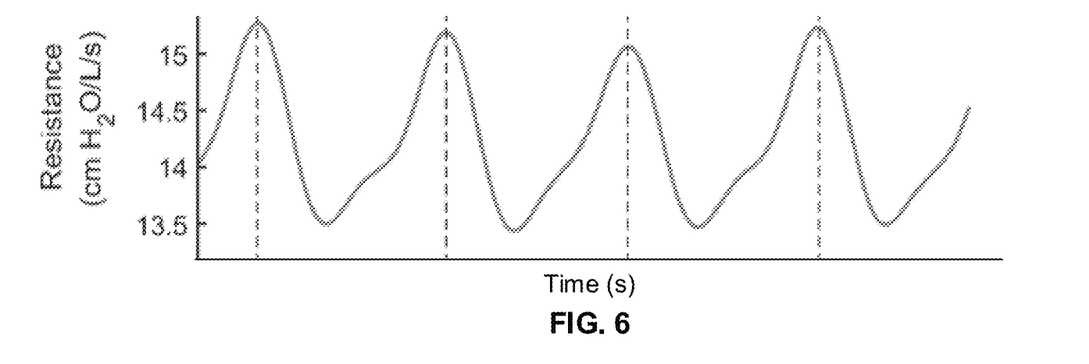
FIG. 6 illustrates measurements of resistance taken at the variable resistance device using an oscillation frequency of 20 Hz for the FOT technique while varying the orifice of the variable resistance device.

Referring now to FIG. 6, shown therein are measurements of resistance taken at the variable resistance device 107 using an oscillation frequency of 20 Hz for the FOT technique while varying the orifice of the variable resistance device 107. The results show that the resistance was successfully varied.

Figure 7:
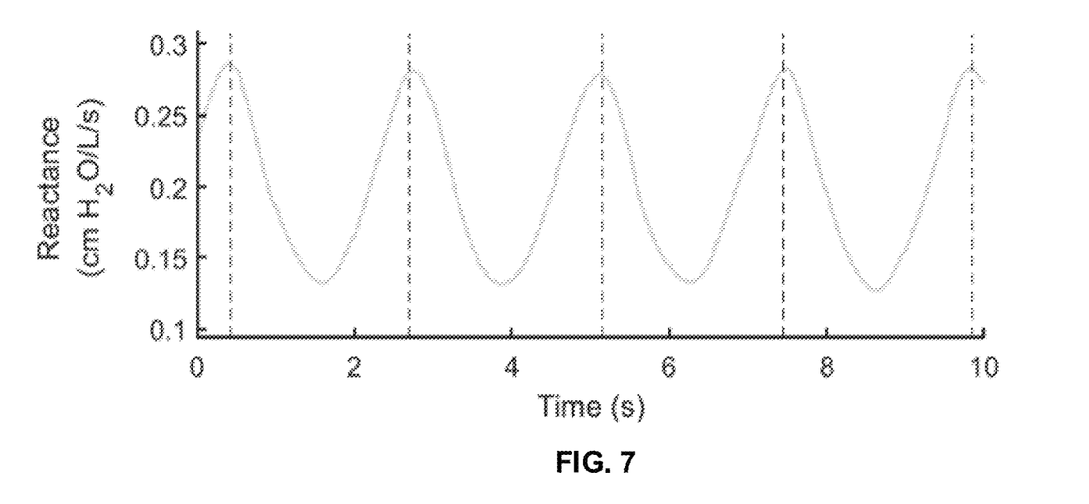
FIG. 7 illustrates measurements of reactance taken at the variable elastance device using an oscillation frequency of 20 Hz for the FOT technique.

Referring now to FIG. 7, shown therein are measurements of reactance taken at the variable elastance device 109 using an oscillation frequency of 20 Hz for the FOT technique. The results show that by varying the pressure of the compliance chamber 405 the compliance was successfully varied.

It should be noted that there can be alternative embodiments in which different elements are used to implement the variable resistance device 107 and/or the variable elastance device 109. For example, different types of motorized orifices may be used in alternative embodiments of the variable resistance device compared to the example embodiments of the variable resistance device that are shown and discussed herein. In addition, different compliance chambers with different shapes and construction can be used in alternative embodiments of the variable elastance device compared to the example embodiments of the variable elastance device that are shown and discussed herein.

It should also be understood that in an alternative embodiment there can be a respiratory system which includes several variable resistance devices and several variable elastance devices where each variable resistance device has unique properties to model different types of lungs and each variable elastance device has unique properties to model different types of lungs. Therefore, during simulation, one of the variable resistance devices and/or one of the variable elastance devices are selected for simulating a particular type of lung model. The different lung models that can be simulated in this fashion include single and multiple branch/compartment models. Multiple sets (i.e. branches) and combinations of the variable resistance and/or variable elastance devices can be built and put in series and/or parallel with each other to simulate different models of the lung.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. A variable resistance device for simulating variations of airway resistance during breathing in a lung simulator, the variable resistance device comprising:
 a single inlet for receiving an input airflow;
 a single outlet for dispelling an output airflow;
 a single channel that is in fluid communication and is physically coupled with the single inlet and the single outlet for receiving the input airflow and providing the output airflow to the single outlet; and
 a time-varying adjustable restrictive element disposed within the single channel and having an orifice that is adjustable to vary a resistance experienced by air that passes through the single channel, wherein the orifice is adjustable during operation of the variable resistance device.

2. The variable resistance device of claim 1, wherein the variable resistance device comprises an iris diaphragm having a plurality of moveable members that define the orifice and are moveable to vary a size of the orifice.

3. The variable resistance device of claim 2, wherein the variable resistance device comprises a motor with a motor output shaft that is coupled to the iris diaphragm for causing the plurality of moveable members to move when the motor output shaft is rotated and the motor output shaft is rotated at a frequency that corresponds to a breathing rate.

4. The variable resistance device of claim 3, wherein the variable resistance device comprises a spur gear with a spur gear channel that is coupled to the motor output shaft, the iris diaphragm comprises a circumferential gear that is coupled to the plurality of moveable members and has a first set of teeth that engage a second set of teeth on the spur gear.

5. The variable resistance device of claim 1, wherein the variable resistance device comprises a flexible airway tube that is coupled to the single inlet and the single outlet and is disposed within the time-varying adjustable restrictive element and a diameter of the flexible airway tube is varied by the time-varying adjustable restrictive element to vary airway resistance.

6. A variable elastance device for simulating elastic properties of a respiratory system, the variable elastance device comprising:
 an airtight chamber;
 an inlet coupled to a first portion of the airtight chamber, the inlet being adapted to receive an input airflow;
 an outlet coupled to a second portion of the airtight chamber, the outlet being adapted for transmitting an output airflow; and
 a flexible membrane disposed within the airtight chamber and being shaped to provide an air pathway between the inlet and the outlet, the flexible membrane separating the airtight chamber into first and second sections that are at first and second pressures, respectively, the first pressure being different from the second pressure, wherein the first and second pressures are varied to adjust an elastance of the variable elastance device.

7. The variable elastance device of claim 6, wherein the variable elastance device comprises a pressure tap for varying the second pressure in the second section.

8. The variable elastance device of claim 6, wherein the first section is internal to the flexible membrane and the second section is external to the flexible membrane and internal to the airtight chamber.

9. The variable elastance device of claim 6, wherein the variable elastance device comprises a stent that is disposed within the flexible membrane and coupled to the inlet and the outlet, the stent having rectangular slots for allowing air to flow towards and away from an inner surface of the flexible membrane causing the flexible membrane to expand and contract.

10. A simulation system for simulating a respiratory system, the simulation system comprising:
 a pressure source for providing input airflow;
 a variable resistance device that is coupled to the pressure source for receiving the input airflow and providing a variable resistance to the input airflow and providing an intermediate airflow, the variable resistance being provided to simulate a variable resistance for the respiratory system during breathing;

a variable elastance device that is coupled to the variable resistance device for receiving the intermediate airflow after and providing a variable elastance to the intermediate airflow and providing an output airflow, the variable elastance being provided to simulate a variation in elastance for the respiratory system during the breathing; and a lung simulator that is coupled to the variable elastance device for receiving the output airflow and adding a volume of air for aiding in simulation of the respiratory system.

11. The simulation system of claim 10, wherein the variable resistance device comprises:
an inlet for receiving the input airflow;
an outlet for dispelling the intermediate airflow;
a channel that is in fluid communication with the inlet and the outlet for receiving the input airflow and providing the intermediate airflow to the outlet; and
a time-varying adjustable restrictive element disposed within the channel and having an orifice that is adjustable to vary the variable resistance experienced by the input airflow that passes through the channel, wherein the orifice is adjustable during operation of the variable resistance device.

12. The simulation system of claim 11, wherein the variable resistance device comprises an iris diaphragm having a plurality of moveable members that define the orifice and are moveable to vary a size of the orifice.

13. The simulation system of claim 12, wherein the variable resistance device comprises a motor with a motor output shaft that is coupled to the iris diaphragm for causing the plurality of moveable members to move when the motor output shaft is rotated and the motor output shaft is rotated at a frequency that corresponds to a breathing rate.

14. The simulation system of claim 13, wherein the variable resistance device comprises a spur gear with a spur gear channel that is coupled to the motor output shaft, the iris diaphragm comprises a circumferential gear that is coupled to the plurality of moveable members and has a first set of teeth that engage a second set of teeth on the spur gear.

15. The simulation system of claim 11, wherein the variable resistance device comprises a flexible airway tube that is coupled to the inlet and the outlet of the variable resistance device and is disposed within the time-varying adjustable restrictive element and a diameter of the flexible airway tube is varied by the time-varying adjustable restrictive element to vary airway resistance.

16. The simulation system of claim 10, wherein the variable elastance device comprises:
an airtight chamber;
an inlet coupled to a first portion of the airtight chamber, the inlet being adapted to receive the intermediate airflow;
an outlet coupled to a second portion of the airtight chamber, the outlet being adapted for transmitting the output airflow; and
a flexible membrane disposed within the airtight chamber and being shaped to provide an air pathway between the inlet and the outlet, the flexible membrane separating the airtight chamber into a first section that is internal to the flexible membrane and a second section that is external to the flexible membrane and internal to the airtight chamber, the first and second sections being at first and second pressures, respectively, the first pressure being different from the second pressure,
wherein the first and second pressures are varied to adjust an elastance of the variable elastance device.

17. The simulation system of claim 16 wherein the variable elastance device comprises:
a pressure tap for varying the second pressure in the second section; and
a stent that is disposed within the flexible membrane and coupled to the inlet and the outlet, the stent having rectangular slots for allowing air in the variable elastance device to flow towards and away from an inner surface of the flexible membrane causing the flexible membrane to expand and contract.

18. The simulation system of claim 10, wherein the variable resistance device is adapted to provide a selected resistance for simulating the respiratory system experiencing a respiratory condition, the variable elastance device is adapted to provide a selected elastance for simulating the respiratory system experiencing the respiratory condition or the variable resistance device is adapted to provide the selected resistance for simulating the respiratory system experiencing the respiratory condition and the variable elastance device is adapted to provide the selected elastance for simulating the respiratory system experiencing the respiratory condition.

19. The simulation system of claim 18, wherein the respiratory condition comprises at least one of asthma, sleep apnea, emphysema and chronic obstructive pulmonary disorder.

20. The simulation system of claim 10, wherein the simulation system comprises multiple branches, each branch comprising the variable resistance device having the variable resistance, the variable elastance device having the variable elastance or the variable resistance device having the variable resistance and the variable elastance device having the variable elastance.

* * * * *